United States Patent [19]

Dunstan et al.

[11] Patent Number: 4,797,624

[45] Date of Patent: Jan. 10, 1989

[54] METHOD AND APPARATUS FOR EDITING PARTICLE PRODUCED ELECTRICAL PULSES

[75] Inventors: Harvey J. Dunstan, Wheathampstead; John G. Harfield, Harlington; Paul Knight; Harvey J. Podgorney, both of Luton, all of England

[73] Assignee: Coulter Electronics, Ltd., Luton, England

[21] Appl. No.: 44,530

[22] PCT Filed: May 30, 1986

[86] PCT No.: PCT/US86/01197

§ 371 Date: Jan. 29, 1987

§ 102(e) Date: Jan. 29, 1987

[87] PCT Pub. No.: WO86/07218

PCT Pub. Date: Dec. 4, 1986

[30] Foreign Application Priority Data

May 31, 1985 [GB] United Kingdom ................ 8513809

[51] Int. Cl.$^4$ .......................... H03K 5/22; H03K 5/00

[52] U.S. Cl. .................... 328/114; 328/115; 328/150; 328/127

[58] Field of Search ............... 328/108, 111, 112, 114, 328/117, 151, 150, 127, 115; 324/71.1, 71.4; 377/10, 11, 12; 307/234, 350, 231

[56] References Cited

U.S. PATENT DOCUMENTS

| | | | |
|---|---|---|---|
| 3,710,264 | 1/1973 | Doty et al. | 377/12 |
| 3,863,160 | 1/1975 | Doty | 328/151 X |
| 3,864,583 | 2/1975 | Fiorino | 328/151 X |
| 4,021,117 | 5/1977 | Göhde et al. | 377/10 |
| 4,694,200 | 9/1987 | Hetyei | 328/117 |

Primary Examiner—Stanley D. Miller
Assistant Examiner—Timothy P. Callahan
Attorney, Agent, or Firm—Gerald R. Hibnick

[57] ABSTRACT

Particle produced pulses are evaluated on an individual basis for shape symmetry, with significantly asymmetric pulses, becoming subject to editing, i.e. exclusion. Pulse symmetry is determined by measuring the areas under the pulse before and after the first pulse amplitude peak and then by comparing those pulse areas with respect to pre-established limits which are not based upon any of the pulses then being evaluated.

19 Claims, 1 Drawing Sheet

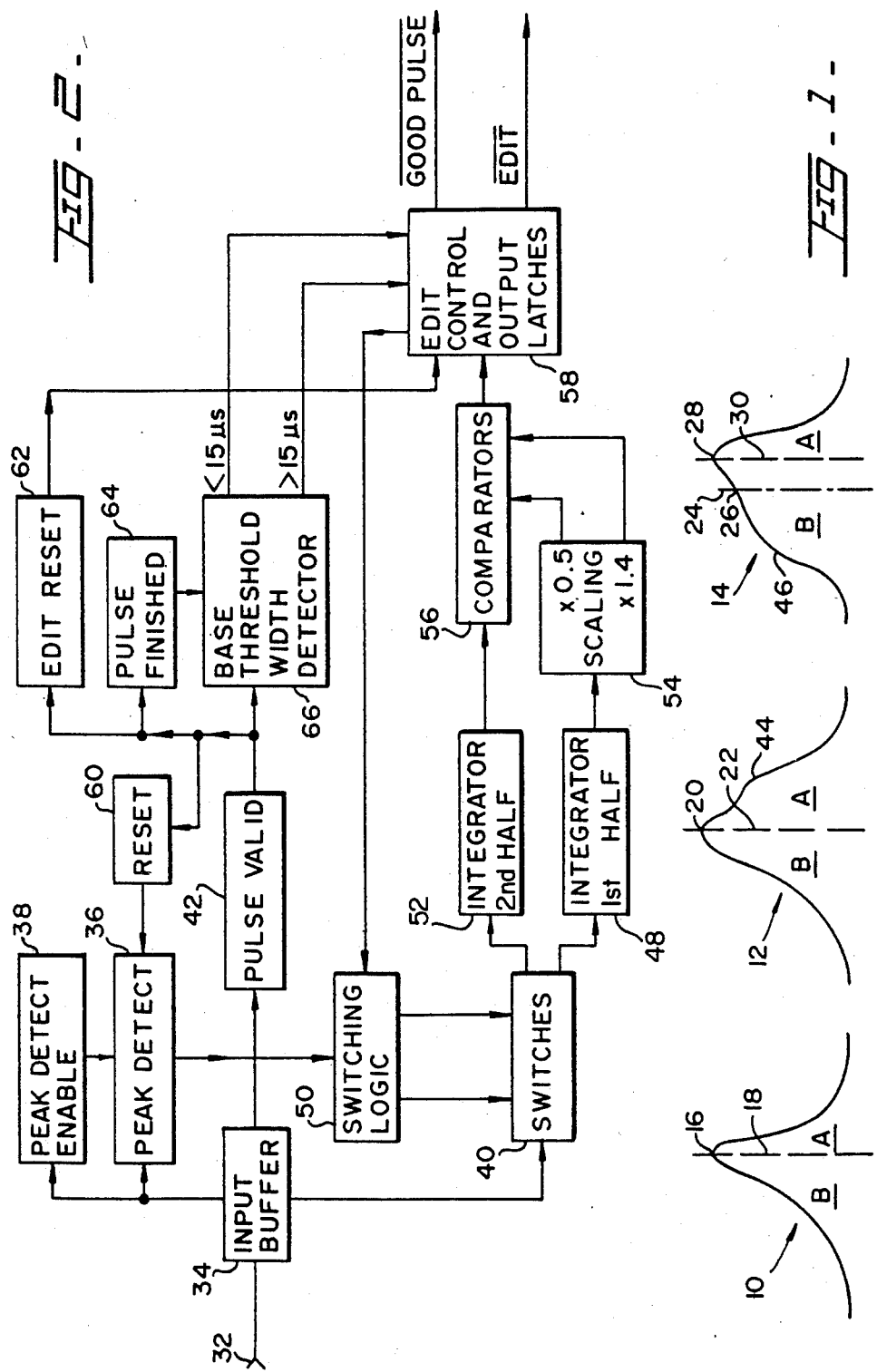

METHOD AND APPARATUS FOR EDITING PARTICLE PRODUCED ELECTRICAL PULSES

This invention concerns the editing, by excluding, of electrical pulses. More specifically, this invention concerns the excluding of certain electrical pulses from a large quantity thereof, which are generated as a result of particle analysis by a particle analyzing apparatus. One general form of such apparatus utilizes the Coulter sensing principle as disclosed in U.S. Pat. No. 2,656,508 and subsequently in numerous improvement patents worldwide. Products employing the Coulter sensing principle are manufactured and now sold by many companies, a primary one of which is Coulter Electronics, Inc. and these are identified by the trademarks Coulter Counter ® and Coulter ®.

According to the Coulter sensing principle, when a microscopic particle in suspension in an electrolyte is passed through an electrical field of small dimensions approaching those of the particle, there will be a momentary change in the electric impedance of the electrolyte in the ambit of the field. This change of impedance diverts some of the excitation energy into the associated circuitry, giving rise to an electrical signal. Such signal has been accepted as a reasonably accurate indication of the particle volume for most biological and industrial purposes. Apparatus embodying the teachings of U.S. Pat. No. 2,656,508 has been used to count and size particles in biological fluids, industrial powders and slurries, etc.

In commercial versions of Coulter particle analyzing apparatuses, the electric field of small dimensions has been formed commonly by a microscopic right cylindrical passageway or aperture, as it is known, between two bodies of liquid in which the particles to be studied are suspended. The electrical excitation energy is coupled to these bodies by means of electrodes respectively located in the liquid bodies, the aperture being formed in an insulating wall between the bodies. The suspension is caused to flow through the aperture, carrying the particles with the flow, and gives rise to the electric signals produced by the momentary changes in impedance caused by the respective particles as they pass through the aperture. The electric field is concentrated in the aperture and normally comprises an electric current flowing through the aperture along with the physical flow of the suspension.

By counting the signals produced, one can count the particles passing through the aperture. By discriminating between different pulse amplitudes, one can make size studies.

The sensing aperture usually is short, that is, its length is the same as or less than its diameter. The optimal particle size-volume information is obtained from the pulse amplitude peak, if that amplitude peak is the result of the particle being in the electrical field approximately halfway through the aperture length and the path of the particle has been along the axis of the aperture. The reason that the pulse peak is optimal when the particle is in the electrical field halfway through the aperture is that such position is most remote from the entrance and exit of the aperture, is most uniform and has the most uniform current distribution for all paths through the aperture. At the entrance and exit of the aperture, the current density is greater at the edges of the aperture and correspondingly lesser on the axis of the aperture. This may be explained by pointing out that current paths other than the axial path are supplied from the sides of the aperture as well as straight ahead. The lower current density on the axis at the entrance and exit results in a lower instantaneous signal than is the case for particles entering the aperture and leaving it on other paths. In other words, the current density at the corners of the aperture is greater than at the axis.

Another reason that axially traversing particles provide optimal pulses is that the velocity of electrolyte flow, and hence the velocity of particles also, is somewhat greater on an axial path than on paths closer to the edges of the aperture or paths which are off-center, because the liquid does not have to change direction when it goes through the axial center of the aperture. The resistance to flow is a minimum on the axis, since it is surrounded by a moving sheath of liquid having substantially the same velocity. Hence, the duration that a particle is flowing through the aperture path can be an indication of whether or not it has followed a primarily axial path, or not. Accordingly, if the pulse duration is used as a basis for discrimination, there can be established criteria for accepting particle produced pulses derived from particles passing on or near axial paths; all other pulses then can be excluded from being analyzed. Such exclusion has been called "editing". Several such editing circuits have been designed and are exemplified in U.S. Pat. Nos. 3,700,867; 3,701,029; 3,710,263; 3,710,264; and 3,783,390. Commercial Coulter Counter analyzers utilizing such editing have been sold for many years and possess distinct advantage over similar analyzers lacking the edit feature.

The problem of locating the center of a pulse amplitude of a particle produced pulse is discussed in U.S. Pat. Nos. 3,668,531 and 3,863,160, and solutions of this problem are presented. Modifying of a particle produced pulse amplitude, when the particle does not traverse the uniform electrical field portions of the aperture path, is taught in U.S. Pat. No. 3,863,159.

Notwithstanding the advantages of the above mentioned prior art, there also have had to be tradeoffs in their implementation as well as their design concepts. The commercialized duration-based edit circuits have utilized the durations of prior pulses of the pulse train as the data base for establishing the nominally acceptable pulse. Hence, if the prior pulses are primarily from particles that traversed the aperture path significantly off axis, their duration will be too long. Also, if the particle concentration is low, then either it will take too long to develop a statistically significant edit criteria, or the criteria might not be based on sufficient data. These just mentioned and other of the design criteria could cause rejection of in fact good pulses, as well as acceptance of too many undesirable pulses. Such conditions might be minimal when the particles are of a relatively narrow size range, such as red or white blood cells; but a greater problem can exist when the particle size distribution is relatively wide, as in industrial particle analysis.

Also to be considered are the cost of the prior art edit circuits and the care by which the circuit parameters are maintained for each analyzer and for different customer needs. Included in the prior art edit circuits are delay circuits and pulse duration memory circuits which contribute to the cost as well as the space requirements of the edit circuits. The most prevalently employed edit circuit also compares the pulse duration at several different percentiles of each pulse and this circuitry further adds to the total cost.

The herein presented invention teaches both method and apparatus for editing electrical pulses derived from particles passing through the sensing aperture of a particle analyzer. This invention seeks to obviate the problems of prior art edit and centerfinding circuits, while achieving suitable pulse editing results, especially for particle populations of relatively wide size volume distributions. The editing criteria is based upon the comparison of the area of the pulse before and after its first peak amplitude. A favorable comparison enables the pulse to be counted and/or sized as a measuring equivalent of the particle from which it was derived. An unfavorable comparison causes that pulse to be edited, i.e. rejected, such that its associated particle is not counted or measured.

Accordingly, the invention provides a method for editing particle produced electrical pulses, said method comprising the steps of: determining the symmetry of each pulse, comparing said symmetry with respect to acceptable limits thereof, and editing each pulse which lies outside of the acceptable symmetry limits.

The invention further provides an apparatus for editing particle produced pulses, said apparatus comprising: pulse symmetry determining means for determining the symmetry of each pulse, symmetry limits defining means for defining pre-established limits of pulse symmetry, comparing means coupled to be responsive to both said pulse symmetry determining means and said symmetry limits defining means for comparing at least one portion of each pulse with respect to pulse symmetry and for generating an output signal indicative of such comparison, said output signal being useful for pulse editing determination.

By way of example, an illustrative embodiment of the invention now will be described with reference to the accompanying drawings in which:

FIG. 1 illustrates three typical pulses for describing the operation of the invention, and FIG. 2 is a block diagram of a preferred embodiment of the electrical circuits of the invention.

With reference to FIG. 1, there are illustrated three pulses 10, 12 and 14. Pulse 10 is an example of an ideal pulse, which results from a particle passing along the axis of the aperture path. The peak 16 is well defined and it separates the area of the pulse into two portions, B—before the peak, and A—after the peak. A dashed vertical line 18, defined by the peak 16 separates these areas B and A, with the area portion B being slightly greater than the area portion A. Pulses of the shape of pulse 10 and close thereto are acceptable and should not be edited by the method and apparatus of the present invention. Unfortunately, only a very small percent of the particles pass along or very near and parallel to the axis of the aperture path. The prior art cited patents illustrate and describe the various and more typical particle paths and the resulting pulses. For example, if particles traversed the aperture parallel to its axis, but along paths increasingly further from the axis, the resulting pulses would have increasingly wider, generally flat-topped peaks and wider bases, with the duration of the areas of portions B and A typically shifting such that the area of A after the peak would become less than one-half of the area B before the peak. Experimental studies, flow models and mathematic development have established that when the particle trajectory is more than sixty percent of the aperture radius out from the aperture axis, then the resulting pulse may require editing.

The pulse 12 and also its mirror image represent a significant percent of the particle pulses which are acceptable. Its peak 20 is slightly higher than the peak 16 of the pulse 10 and is not as close to the pulse-duration center, as seen by the vertical line 22. The peak 20 is higher than the peak 16, since the particle 12 was off axis at that time, but then came closer to and more parallel to the axis as it progressed further through the aperture path. The after peak area A is greater than the before peak area B, but not so much that this pulse requires edit rejecting.

The pulse 14 and its mirror image also represent a significant percent of typical particle generated pulses; however, these pulses are not acceptable and should be edited, since their amplitudes 26, proximate their time centers as represented by the centerline 24, do not closely enough represent the particle volume. The areas B and A of the pulse 14, as defined by the peak 28 and the resulting vertical line 30, are significantly not equal, with the area B being more than 1.4 that of the area A. The pulse 14 therefore is nonsymmetric to too great an extent. In contrast, the pulses 10 and 12 also are nonsymmetric, but within acceptable limits. The time center lines of the pulses 10 and 12 and the peaks thereon are not illustrated, since they lie quite close to the verticals 18 and 22 and the peaks 16 and 20; in fact for pulses 12 they are coincident.

From the above discussion of the pulses 10, 12 and 14 and their respective areas B and A, there now should be appreciated that the flow dynamics and electrical field in and around a sensing aperture of a particle analyzer utilizing the Coulter principle determine the symmetry of the pulses and the pulse areas B and A and that editing criteria might be derived therefrom. This in fact is true and is the basis of the present invention. The generalized formula $Y<A<Z$ represents the area range of area A relative to area B and is verbalized as: if the area of A is greater than the area B times a factor Y, but is no greater than the area B times a factor Z, then the particle pulse is acceptable. Pulses lying outside these acceptable limits of A should be edited, i.e. excluded or rejected. When utilizing a particle analyzer sold under the trademark Coulter Counter, experimental data developed the limit establishing values of Y and Z to be, respectively, 0.5 and 1.4; hence, the resulting formula $0.5B<A<1.4B$ is the relationship of the pulse areas B and A, with values ±10% for Y and Z being acceptable.

It should be noted carefully that, since particle analyzers employing the Coulter principle are not all made by Coulter Electronics, Inc. or its related companies, the electrical supplies and parameters, flow dynamics, and diameter to length ratio of the aperture path are not all in conformity with Coulter Counter analyzers. Hence, the values of Y and Z can be different from manufacturer to manufacturer and possibly from instrument to instrument, if quality control is not of high standard. Thus, it might be necessary to evaluate a particle analyzer to establish the values of Y and Z for it. Also, certain unique customer needs and particle populations could cause the values of Y and Z to need to be adjusted. Such determinations, evaluations and adjustments are well within the skill in the art. In fact, the design of an edit circuit, based upon the now herein presented invention, now also should be within the skill of the art.

FIG. 2 illustrates an electrical block diagram of a preferred embodiment of a circuit for practicing the invention. Each of the circuit blocks are of basic, known design; therefore, their function and operation will be described only to the extent necessary for the reader to become better acquainted with the invention.

The particle pulse, which is derived from the sensing aperture and its electrodes, is applied to an input terminal 32 of an input buffer 34. The input buffer feeds the pulse to a peak detect element 36, its peak detect enable 38, a switches unit 40, and a pulse valid block 42. The pulse valid block can be a typical threshold circuit which passes only that portion of the pulse which exceeds a minimum acceptable threshold value, such as 30 millivolts. The peak detect can be a typical sample and hold circuit, which "follows" the pulse until it detects a "true" or resolved peak. A resolved peak is one that has an amplitude greater than the amplitude just prior to and just after it, such as the peaks 16, 20 and 28 in FIG. 1. In contrast, an unresolved peak, such as 44 and 46 in pulses 12 and 14, would not be detected. Any second true peak will not be analyzed, by virtue of timing and reset boxes in FIG. 2, or capable of being present. During the time that the area B—before the peak—is being followed by the peak detect element 36, that pulse portion B is fed by the input buffer 34 to the switches 40 and from there to a first half pulse integrator 48. When the first true peak is detected, the peak detect 36 so advises a switching logic element 50, which then switches its output to the switches unit 40 to cause the output from the buffer 34 to feed the pulse portion A—after the peak—to a second half pulse integrator 52. The integrated area B signal then is applied to a scaling circuit 54, which provides the Y=x0.5 and the Z=x1.4 scaling factors to the area value B, for comparison in a comparators unit 56 with the integrated area A. If the $0.5B < A < 1.4B$ criteria is met, then a favorable symmetry comparison signal is fed to an edit control and output latches circuit 58. If the comparison fails, then the comparators unit 56 emits an edit or reject signal to the edit control circuit 58. The peak detect, switches and integrators can be said to comprise pulse symmetry determining means. The scaling circuit is a symmetry limits defining means which includes pre-set means for fixing the pre-established limits.

Although a favorable symmetry comparison of the area A to the area B is the primary feature of this invention, it does not of and by itself enable a good pulse output from the edit control and output latches circuit 58, because of other practical needs to be considered. There are three more inputs to that circuit 58 which must be satisfied. Returning to the valid pulse unit 42, its output is coupled to: a reset element 60 for the peak detect 36; an edit reset block 62, which feeds into the edit control circuit 58; a pulse finished unit 64, which feeds into a base threshold width detector 66; and the pulse valid also is coupled directly into that same base threshold width detector. Assuming a particle pulse and not a small, low voltage pulse causing condition, the pulse valid output will be affirmative and be capable of being duration measured by the base threshold width detector 66. Such width is at a minimum threshold set by the pulse valid circuit, such as 30 millivolts. The width detector 66 establishes a simple width criteria, in this example, less than or greater than 15 microseconds, which is a nominal value for a Coulter Counter analyzer. Such value is preset based on manufacturer's knowledge. It is not intended to be: a primarily variable parameter, not dynamic, nor based upon recent pulse duration history, as in the prior art. If the system input signal at the terminal 32 is a particle pulse and not a noise spike or the like, the pulse width duration should be favorably met, i.e. more than 15 us, and that pulse is cleared through the output latches of the circuit 58, assuming that pulse valid and comparators signals also are favorable.

The terms "positive, negative, true and false" have not been used hereinabove, nor "leading edge trigger", or "trailing edge responsive", nor "high", or "low" with respect to signals, polarity, etc., since signal inversion in or between stages for amplification or logic control would tend to make those terms confusing or limiting in the example of FIG. 2. In fact, and as shown at the right end of FIG. 2, the output signals in the commercially designed edit system are inverted, such that the unedited or desirable output particle pulses are identified as "edit not"; whereas, the rejected or edited output pulses are noted as "good pulse not".

The contents and functions of circuit blocks of FIG. 2 should be understood by those skilled in the art. It should be noted that the two integrators can be matched by applying a bell shaped pulse of fixed height to the input terminal 32 and then by adjusting a variable resistor at the input of one of the integrators, such as 52, until the output of the integrators 48 and 52 are within ±1%.

Now therefore, there has been discussed and illustrated the basic concepts of the present invention—discrimination based upon pulse symmetry of each individual pulse itself, not upon an average value, nor upon a recent history of pulse duration and percentiles; no use of delay lines, and substantial independence of circuit induced variations and flow rate changes. Low concentrations of particles can be analyzed, even in the presence of significant amounts of debris and cell stroma. The area under the pulse is divided into two portions B and A—before the first peak and after that peak. If the ratio of the two areas falls within the limits $YB < A < ZB$, then the particle pulse should be acceptable with respect to its symmetry.

The embodiments of the invention in which an exclusive property or privilege is claimed are defined as follows:

1. A method for editing particle produced electrical pulses, said method comprising the steps of: determining the symmetry of each pulse, comparing said symmetry with respect to acceptable limits thereof, and editing each pulse which lies outside of the acceptable symmetry limits.

2. The method according to claim 1 in which said step of determining the symmetry is accomplished by measuring the areas of different portions of a pulse.

3. The method according to claim 2 in which said areas are of two different pulse portions which lie on opposite sides of a peak amplitude of the pulse.

4. The method according to claim 3 in which said peak amplitude is the first peak amplitude of the pulse.

5. The method according to any one of claims 1, 2, or 3 including the step of establishing said acceptable limits in a manner which is not based upon any pulse being processed by this method.

6. The method according to any one of claims 2, 3, or 4 in which said step of comparing compares the different pulse portion areas with respect to said acceptable limits.

7. The method according to claim 1 in which said acceptable limits are defined by the general formula $YB < A < ZB$, in which A is the area of one portion of the pulse, and YB and ZB are equal to B, the area of an other portion of the pulse, multiplied by different constants.

8. The method according to claim 7 in which Y approximates 0.5 and Z approximates 1.4.

9. The method according to claim 7 in which the area A lies on one side of the peak amplitude of the pulse.

10. The method according to any one of claims 7, 8, or 9 in which the area A is the area of the pulse which develops after the first peak of the pulse.

11. The method according to any one of claims 7, 8, or 9 in which B is the area of said other portion of the pulse and is developed before the first peak of the pulse for comparing with the area limits of the area A.

12. The method according to any one of claims 1, 2, or 7 which has the additional step of comparing each pulse with a pre-established minimal acceptable width at a threshold amplitude, whereby any pulse failing to exceed this pre-established minimal width cannot succeed in passing through this method for editing.

13. The method of any one of claims 1, 2, or 7 further comprising the step of generating said pulse by use of the Coulter principle.

14. An apparatus for editing particle produced pulses, said apparatus comprising: pulse symmetry determining means for determining the symmetry of each pulse, symmetry limits defining means for defining pre-established limits of pulse symmetry, comparing means coupled to be responsive to both said pulse symmetry determining means and said symmetry limits defining means for comparing at least a portion of each pulse with respect to pulse symmetry and for generating an output signal indicative of such comparison, said output signal being useful for pulse editing determination.

15. The apparatus according to claim 14 in which said pulse symmetry determining means measures the area of two different portions of the pulse and feeds one of the area portions directly to said comparing means, and said symmetry limits defining means is interposed between said pulse symmetry determining means and said comparing means for receiving the other of the area portions and scaling it with respect to the pre-established symmetry limits prior to comparison by said comparing means.

16. The apparatus according to claim 15 in which said pulse symmetry determining means includes pulse peak detecting means which defines the two different pulse portions as said one being that which is after the pulse peak and said other being that which is before that pulse peak.

17. The apparatus according to claim 15 or 16 in which said symmetry limits defining means includes scaling means operative with the form $YB<A<ZB$, in which:

A is the area of the one pulse portion,

Y approximates 0.5, and

Z approximates 1.4;

whereby the thus scaled value of the area B is compared with the area A, which is the area of said one pulse portion.

18. The apparatus according to any one of claims 14, 15, or 16 in which said symmetry limits defining means includes pre-set means for fixing the pre-established limits such that those limits are not influenced by pulses being processed by said apparatus.

19. The apparatus according to any one of claim 14, 15, or 16 in which said particle produced pulses are generated by particles passing through sensing aperture means operating according to the Coulter principle.

* * * * *